(12) United States Patent
Zamudio Rivera et al.

(10) Patent No.: US 9,981,958 B2
(45) Date of Patent: May 29, 2018

(54) OXAZOLIDINES DERIVED FROM POLYALKYL OR POLYALKENYL N-HYDROXYALKYL SUCCINIMIDES, OBTAINMENT PROCESS AND USE

(75) Inventors: Luis Silvestre Zamudio Rivera, Mexico City (MX); Eugenio Alejandro Flores Oropeza, Mexico City (MX); Marcelo Lozada y Cassou, Mexico City (MX); Hiram Isaac Beltran Conde, Mexico City (MX); Eduardo Buenrostro Gonzalez, Mexico City (MX); Youri Douda, Mexico City (MX); Mario Alberto Guzman Vega, legal representative, Mexico City (MX); Adela Morales Pacheco, Mexico City (MX); Violeta Yasmin Mena Cervantes, Mexico City (MX); Raul Hernandez Altamirano, Mexico City (MX)

(73) Assignee: Instituto Mexicano Del Petroleo, Mexico City (MX)

( * ) Notice: Subject to any disclaimer, the term of this patent is extended or adjusted under 35 U.S.C. 154(b) by 899 days.

(21) Appl. No.: 12/596,062

(22) PCT Filed: Apr. 15, 2008

(86) PCT No.: PCT/MX2008/000052
§ 371 (c)(1),
(2), (4) Date: Oct. 15, 2009

(87) PCT Pub. No.: WO2008/130214
PCT Pub. Date: Oct. 30, 2008

(65) Prior Publication Data
US 2010/0107478 A1 May 6, 2010

(30) Foreign Application Priority Data
Apr. 18, 2007 (MX) .................... MX/a/2007/004651

(51) Int. Cl.
*C07D 413/06* (2006.01)
*C10L 1/2383* (2006.01)
*C10L 10/04* (2006.01)

(52) U.S. Cl.
CPC .......... *C07D 413/06* (2013.01); *C10L 1/2383* (2013.01); *C10L 10/04* (2013.01)

(58) Field of Classification Search
CPC .. C10L 1/22; C10L 1/221; C10L 1/222; C10L 1/232; C10L 1/2222; C07D 209/00; C07D 221/00; C07D 413/02
(Continued)

(56) References Cited

U.S. PATENT DOCUMENTS 3,361,673 A 1/1968 Stuart et al.
3,455,831 A 7/1969 Davis
(Continued)

FOREIGN PATENT DOCUMENTS

DE 10123553 11/2002
ES 2002426 8/1988
(Continued)

OTHER PUBLICATIONS

Al-Masum, M. et al., An Efficient Reaction Process for the Synthesis of Oxazinanes, and Oxazolidines in the Presence of Air, International Journal of Organic Chemistry, 2012, 2, 362-365.
Bergmann, E. et al., The Structure of the Products of Condensation between Primary Beta-Hydroxyamines and Aliphatic Carbonyl Compounds, J. Am. Chem. Soc., 1953, 75(2), 358-361.
Gandhi, S. et al., Studies on the Reaction of Aziridines with Nitriles and Carbonyls: Synthesis of Imidazolines and Oxazolidines, J. Org. Chem., 2007, 72, 2133-2142.
Godinez-Salomon, F. et al., Strecker intermediates as non-pollutant scavengers for cyanides, Green Chem., 2005, 7, 716-720.
Johansen, M. et al., Prodrugs as drug delivery systems XXV: Hydrolysis of oxazolidines—a potential new prodrug type, J. Pharm. Sci., 1983, 72(11):1294-8 (Abstract).
Just, G. et al., A simple synthesis of oxazolidine and thiazolidine derivatives of hydroxymethylglyceraldehyde acetonide, J. Org. Chem., 1976, 38, 1534-1538.
(Continued)

*Primary Examiner* — Ellen M McAvoy
*Assistant Examiner* — Ming Cheung Po
(74) *Attorney, Agent, or Firm* — Dickinson Wright, PLLC

(57) ABSTRACT

Oxazolidines, a process for producing the oxazolidines, and use as additives for fuels to prevent and control deposits in internal combustion engines are disclosed. The oxazolidines are derived from polyalkyl or polyalkenyl N-hydroxyalkyl succinimides and have the structural formula

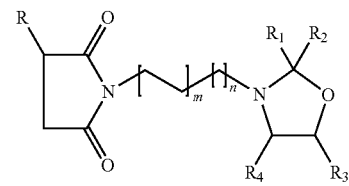

wherein:
R is a polyakyl or polyalkenyl group having an average molecular weight ranging from 450 to 5000 daltons;
m is an integer between 1 and 5;
n is an integer between 0 and 1; and
$R_1$, $R_2$, $R_3$, and $R_4$ are independent radicals, represented by the groups: —H, —$CH_2(CH_2)_4B$, —$C_6H_3DE$ or —$C_{10}H_4FG$; wherein:
A is an integer between 0 and 8,
B is a group selected among —H, —$NH_2$, —OH, —COOH, and
D, E, F, and G are independent radicals, selected among the groups: —H, —$CH_3$, —$CH_2CH_3$, —$CH_2CH_2CH_3$, —$CH_2(CH_2)_2CH_3$, —$(CH_3)_3$, $C_6H_5$, —$NH_2$, —OH, —$OCH_3$, $OCH_2CH_2OH$, $OCH(CH_3)CH_2OH$, $OC_6H_5$—COOH, and —$SO_3$.

22 Claims, No Drawings

(58) Field of Classification Search
USPC .......................................................... 44/341
See application file for complete search history.

(56) References Cited

U.S. PATENT DOCUMENTS

| | | | |
|---|---|---|---|
| 3,455,832 A | | 7/1969 | Davis |
| 3,502,677 A | | 3/1970 | Suer |
| 3,658,836 A | | 4/1972 | Vineyard |
| 4,049,564 A | * | 9/1977 | Ryer .................... C07D 263/12 44/341 |
| 4,066,433 A | * | 1/1978 | Hunsucker ........... C07D 263/04 504/156 |
| 4,277,353 A | * | 7/1981 | Deen .................... C07D 263/04 252/392 |
| 4,471,091 A | * | 9/1984 | Hayashi ................ C08F 255/08 508/452 |
| 4,699,724 A | | 10/1987 | Nalesnik et al. |
| 4,897,086 A | | 1/1990 | Blain et al. |
| 5,393,309 A | | 2/1995 | Cherpeck |
| 5,916,825 A | | 6/1999 | Cherpeck |
| 5,954,843 A | | 9/1999 | Cherpeck |
| 5,962,378 A | * | 10/1999 | Tiffany .................... C10L 1/143 44/347 |
| 5,993,497 A | | 11/1999 | Cherpeck et al. |
| 6,352,566 B1 | | 3/2002 | Cherpeck |
| 6,676,715 B2 | | 1/2004 | Henry et al. |
| 6,800,596 B1 | | 10/2004 | Loper |
| 2004/0180797 A1 | | 9/2004 | Huffer et al. |

FOREIGN PATENT DOCUMENTS

| | | |
|---|---|---|
| MX | 169701 | 7/1993 |
| MX | 184538 | 4/1997 |
| MX | 9710418 | 6/1999 |
| MX | 9805485 | 1/2000 |
| MX | 9500573 | 2/2002 |
| MX | 234498 | 2/2006 |
| WO | 9725392 | 7/1997 |

OTHER PUBLICATIONS

Khrustalev, D.P. et al., Synthesis of 2-Substituted-1,3-oxazolidines under Microwave Irradiation, Russian Journal of General Chemistry, 2007, vol. 77, No. 5, p. 969.
Shaghafi, M. et al., Oxazolidine Synthesis by Complementary Stereospecific and Stereoconvergent Methods, Org. Lett., 2011, 13(19), pp. 5188-5191.
*Streker Intermediates as Non-pollutant Scavengers for Cyanides*, Fernando Godinez-Salmon, Jose M. Hallen-Lopez, Herbert Höpfl, Adela Morales-Pachecho, Hiram I. Beltran and Luis S. Zamudio-Rivera. The Royal Society of Chemistry, Greem Chm., 2005, 7, 716-720. Published as an Advance Article on the web Aug. 30, 2005, DOI: 10.1039/b504406e.www.rsc.org/greenchem Green Chemistry.
*Adsorption of poly(isobutenylsuccinimide) dispersants at a solid-hydrocarbon interface.* Y. Chevalier, M.-C. Dubois-Clochard, J. P. Durand, B. Delfort, P. Gateau, L. Barre, D. Frot, Y. Briolant, I. Blanchard, and R. Gallo. Structure and Dynamics at Interfaces. Pror Colloid Polym Sci (2001) 118: 110-114 @ Springer-Verlag 2001.
*Development of Multifunctional Detergent-Dispersant Additives Based on Fatty Acid Methyl Ester for Diesel and Biodesel Fuel.* Adam Beck, Mark Bubalik and Jeno Hancsok, University of Pannonia, MOL Hydrocarbon and Coal Processin Department, Hungary. www.intechopen.com.
*Exploiting Chemical Diversity for Drug Discovery.* Edited by Paul A. Bartless and Michael Entzeroth, RSC Biomolecular Sciences.
*Experimental and QSPR Studies on the Effect of Ionic Surfactants on n-Decane-Water Interfacial Tension.* Mojtaba Fallah Fini, Siavash Riahi, Alireza Bahramian, Springer AOCS 2012, J. Surfact Deterg (2012) 15:477-484 DOI 10.1007/s11743-012-1330-7. Jan. 12, 2012/Published online Feb. 2, 2012.
Polyisobutylene (PIC)-Based Fuel Additives, Chevron-Oronite Company LLC, Product Stewardship Summary, www.oronitegoes.com Feb. 2012.

* cited by examiner

OXAZOLIDINES DERIVED FROM POLYALKYL OR POLYALKENYL N-HYDROXYALKYL SUCCINIMIDES, OBTAINMENT PROCESS AND USE

TECHNICAL FIELD OF THE INVENTION

The present invention relates to oxazolidines derived from polyalkyl or polyalkenyl N-hydroxyalkyl succinimides, the obtainment process thereof, and their use to prevent and control the formation of deposits in internal combustion engines, primarily in formulations of additives to be applied to hydrocarbon fuels.

BACKGROUND OF THE INVENTION

The formation of deposits in internal combustion engines due to the oxidation and polymerization of hydrocarbon fuels is a well known problem worldwide. Such a problem results in an increase in both fuel consumption and emission of toxic gases to the atmosphere. The components of the engine where the deposits are more likely to build-up depend on the type of engine used. The components that most commonly show this problem include: carburetors, injectors, intake valves, and combustion chamber.

Traditionally, the formation of deposits in internal combustion engines has been controlled by using detergent dispersant additives for fuels, which are comprised of two essential parts, generically known as head and tail. The head has heteroatoms, high in electronic density, which adhere to a metallic surface through coordination bonds, as its essential feature, whereas the tail's main feature is that of being constituted by branched aliphatic chains, which are able to dissolve the deposits that build-up during the combustion process.

The polyisobutenyl succinimides, the polyisobutylene amines, and the polyisobutenyl phenols are some of the most important families of compounds that have been used as dispersant detergents for fuels over the past two decades. In recent years, one of the main interests worldwide has been the optimization of these three compound families' chemical structure, as well as finding chemical substances that, in combination with them, exert synergistic effects that reflect on the efficiency to decrease deposits with lower doses.

As important examples in the literature mentioning the development of polyisobutenyl succinimides and its use on additives for fuels and lubricating oils, we can quote the following international patent documents: U.S. Pat. No. 6,352,566 B1 U.S. Pat. No. 5,993,497; U.S. Pat. No. 5,954,843; U.S. Pat. No. 5,916,825; U.S. Pat. No. 5,393,309; WO 97/25,392; U.S. Pat. No. 6,676,715 B2; U.S. Pat. No. 6,800,596 B1; U.S. Pat. No. 4,87,086; and DE 101 23 553 A1;
as well as the national patent documents: MX 234498, MX 169701, MX 184538, 500573, 9710418, and 9805485.

The U.S. Pat. No. 6,352,566 B1 patent refers to the development of ethers of polyalkyl or polyalkenyl N-hydroxyalkyl succinimides having the structural formula

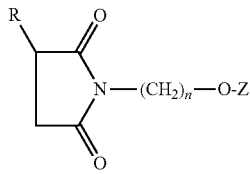

(1)

and their use in additives for fuels that prevent and control the formation of deposits in engines.

In the structural formula (I):
R is a polyalkyl or polyalkenyl group with an average molecular weight of 450 to 5000;
n is an integer from 2 to 5; and
Z is a moiety selected from the groups

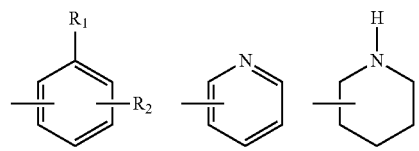

(2)

The U.S. Pat. No. 5,993,497 patent refers to the development of esters of polyalkyl or polyalkenyl N-hydroxyalkyl succinimides having the structural formula

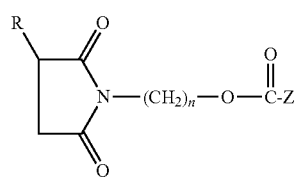

(3)

and their use in additives for fuels that prevent and control the formation of deposits in engines.

In the structural formula (3):
R is a polyalkyl or polyalkenyl group with an average molecular weight of 450 to 5000;
n is an integer from 2 to 5; and
Z is a moiety selected from the groups referred in (2), same as used by the U.S. Pat. No. 6,352,566 B1 patent.

The U.S. Pat. No. 5,954,843 patent refers to the development of aminocarbamates of polyalkyl or polyalkenyl N-hydroxyalkyl succinimides having the structural formula

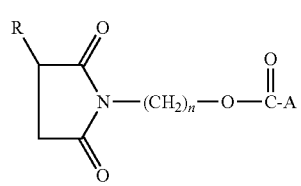

(4)

and their use in additives for fuels that prevent and control the formation of deposits in engines.

In the structural formula (4):
R is a polyalkyl or polyalkenyl group with an average molecular weight of 450 to 5000;
n is an integer from 2 to 5; and
A is part of a polyamine having at least one basic nitrogen atom, wherein the polyamine is bound to the carbonyl group through one of its nitrogen atoms in order to form the corresponding carbamate group.

The U.S. Pat. No. 5,916,825 patent refers to the development of polyisobutanyl succinimides having the structural formula

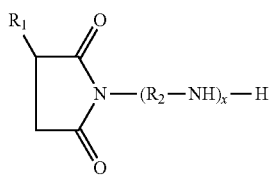

(5)

and their use in additives for fuels that prevent and control the formation of deposits in engines.

In the structural formula (5):

$R_1$ is a highly reactive polyisobutylene-derived polyisobutanyl group with an average molecular weight ranging from 500 to 5000;

$R_2$ is an alkylene group of 2 to 6 carbon atoms; and x is an integer from 1 to 4.

The U.S. Pat. No. 5,393,309 patent refers to the development of an additive composition for fuels, which contains a diethylene diamide- or diethylene triamide-derived polyisobutenyl succinimide having the structural formula

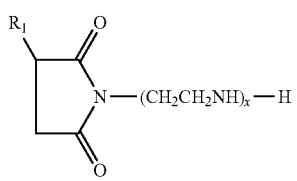

(6)

wherein:

R is a polyisobutenyl group with an average molecular weight of 1200 to 1500, and x adopts the value of 1 or 2.

The WO 97/25,392 patent refers to the development of a detergent composition for gasolines, based on a polyisobutenyl succinimide, obtained from the reaction of either a polyisobutenyl succinic anhydride or a polyisobutenyl succinic acid with a polyalkylene polyamine. The polyisobutenyl group generally has a molecular weight ranging from 500 to 5000, preferably from 800 to 1300. The polyalkylene polyamine used has the structural formula

   (7)

wherein:

R is an alkylene radical of 1 to 5 carbon atoms, and x is an integer from 1 to 10.

The U.S. Pat. No. 6,676,715 B2 patent refers to the use of polyisobutenyl succinimides, preferably the monotetraethylene-pentaamine polyisobutenyl succinimide, as thermostabilizers for cetane-boosters used in diesel.

The U.S. Pat. No. 6,800,596 B1 patent refers to the development of a new dispersant for lubricant oils with enhanced properties. The product is prepared by crossing-over a succinimide with a polyphenolic compound under Mannich-type reaction conditions. The structural formula of one of the families of compounds protected in this patent is

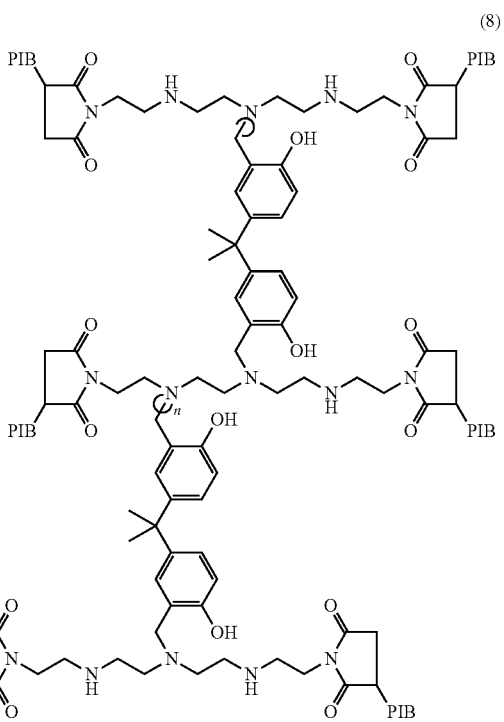

(8)

The U.S. Pat. No. 4,897,086 patent refers to the development of an additive for liquid hydrocarbon fuels, particularly to be applied on diesel and lubricants. The additive is constituted by the reaction product of polyalkenyl-substituted succinimides, aldehydes and triazoles. The polyalkenyl-substituted succinimide used in the reaction has the structural formula

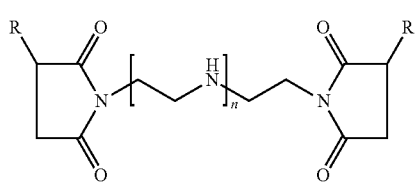

(9)

and the reaction product protected in the patent is

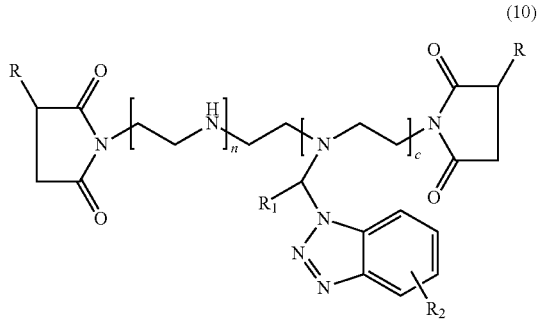

(10)

wherein:
R is an alkenyl or alkyl group of 9 to 150 carbon atoms,
$R_1$ and $R_2$ are each hydrogen atoms or an alkyl, aryl, arylalkyl, or alkylaryl group of 1 to 12 carbon atoms,
c is an integer value greater than 0, and
n+c is an integer value between 1 and 4.

The US 2004/0180797 A1 patent, equivalent to the DE 101 23 553 A1 patent published in Germany, describes a method to produce polyalkenyl succinimides, particularly polyisobutylene succinimides, and the application of these type of products in multi-functional additives for fuels. The polyisobutylene succinimides obtained are produced by the reaction of a polyisobutenyl succinic anhydride with a polyamine, having the structural formula

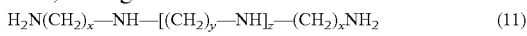

$$H_2N(CH_2)_x—NH—[(CH_2)_y—NH]_z—(CH_2)_xNH_2 \quad (11)$$

in presence of an alcohol or phenol.
In the structural formula (11):

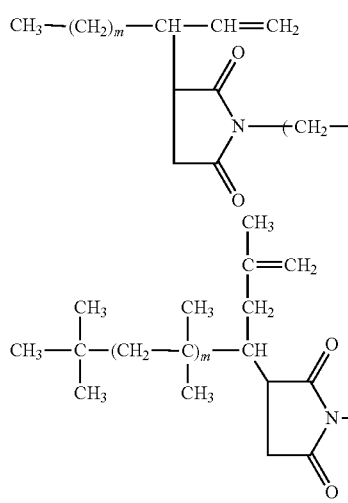

x and y are independent numbers from 1 to 5, preferably from 2 to 4; and
z is an integer from 0 to 8.

The MX 234498 national patent refers to the development of a new detergent-dispersant additive formulation for automobile gasoline and lubricant oils, with enhanced detergency, dispersion, and antioxidant properties. This formulation consists essentially of the mixture of a hydroxylated polyisobutylene sucinimide and a polyether derived from the propylene oxide of the structures (12)

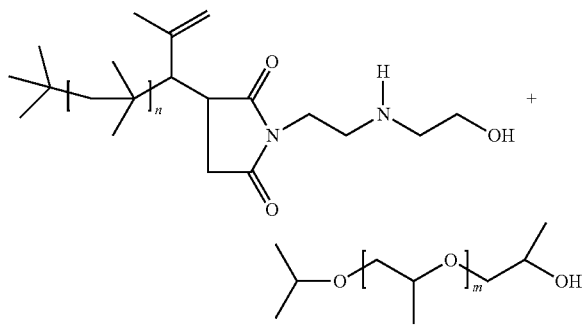

wherein:
n is an integer from 14 to 24, and
m is an integer from 14 to 28.

The national MX 169701, MX 184538, 9500573, and 9710418 patent documents refer to the development of multi-functional additives for gasoline based on polyisobutylene succinimide. The concentration in weight % of the polyisobutylene succinimide in these patent documents is 45-55, 50-60, 30-40, and 20-95 wt. %, respectively, and the structural characteristics of the polyisobutylene succinimide used are never established or even mentioned.

The 9805485 national patent application refers to a procedure for preparing poly-alpha-olefin succinimides by means of a known synthetic pathway and their use as dispersant detergent-active ingredients in multi-functional additives formulations. The general structures proposed for the poly-alpha isobutylene succinimides derivatives are:

(13)

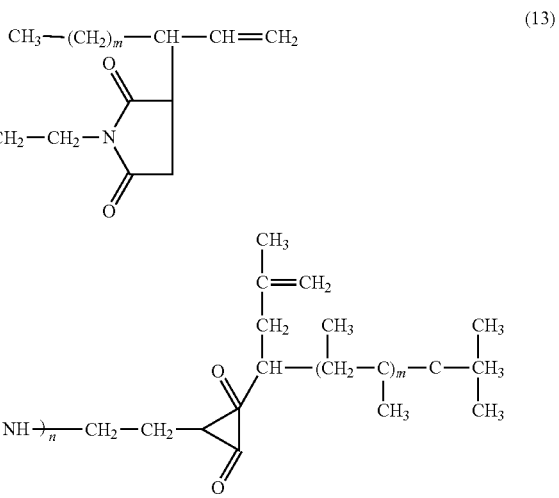

Previous technologies known by the applicant were surpassed by means of the present invention, which relates to oxazolidines derived from polyalkyl or polyalkenyl N-hydroxyalkyl succinimides, the obtainment process thereof, and their use to prevent and control the formation of deposits in internal combustion engines.

One of the main objectives of the present invention is, therefore, to provide a novel structure of new oxazolidines derived from polyalkyl or polyalkenyl N-hydroxyalkyl succinimides.

A further aim of the present invention is to supply prevention and control of deposit build-ups in internal combustion engines as the primary use for the oxazolidines derived from polyalkyl or polyalkenyl N-hydroxyalkyl succinimides, especially in formulations of additives to be applied to hydrocarbon fuels.

DESCRIPTION OF THE INVENTION

The present invention relates to oxazolidines derived from polyalkyl or polyalkenyl N-hydroxyalkyl succinimides, the obtainment process thereof, and their use in order to prevent and control the formation of deposits in internal combustion engines, primarily in formulations of additives to be applied to hydrocarbon fuels.

The oxazolidines derived from polyalkyl or polyalkenyl N-hydroxyalkyl succinimides of the present invention have the structural formula

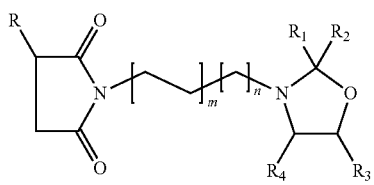

wherein:
R is a polyalkyl or polyalkenyl group with an average molecular weight ranging from 450 to 5000 daltons;
m is an integer between 1 and 5;
n is an integer between 0 and 1; and
$R_1$, $R_2$, $R_3$, and $R_4$ are independent radicals, represented by the groups: —H, —$CH_2(CH_2)_4$B, —$C_6H_3$DE or —$C_{10}H_4$FG; wherein:
A is an integer between 0 and 8,
B is a group, selected among —H, —$NH_2$, —OH, —COOH, and
D, E, F and G are independent radicals, selected among the groups: —H, —$CH_3$, —$CH_2CH_3$, —$CH_2CH_2CH_3$, —$CH_2(CH_2)_2CH_3$, —$(CH_3)_3$, $C_6H_5$, —$NH_2$, —OH, —$OCH_3$, $OCH_2CH_2OH$, $OCH(CH_3)CH_2OH$, $OC_6H_5$—COOH, —$SO_3$.

The oxazolidines derived from polyalkyl or polyalkenyl N-hydroxyalkyl succinimides of the present invention are highly efficient as additives that prevent and control the formation of deposits in internal combustion engines.

The oxazolidines derived from polyalkyl or polyalkenyl N-hydroxyalkyl succinimides, object of the present invention, were prepared according to the following synthesis pathway:

The polyalkyl or polyalkylene succinic anhydride to 2-(aminoalkylamino)-2,3-disubstituted-alcohol molar ratio ranges from 1:1 to 1:10, preferably from 1:1 to 1:4, with the reaction being carried out in the bulk substance or in the presence of an inert hydrocarbon solvent, preferably toluene, mixtures of xylene, o-xylene, m-xylene, p-xylene, kerosene, and turbo-fuel. The reaction time depends on the structure of the polyalkyl or polyalkylene succinic anhydride and the 2-(aminoalkylamino)-2,3-disubstituted-alcohol used as reactants, as well as on the temperature at which the reaction is carried out. Generally, the reaction time ranges from 1 to 24 hours, preferably from 1 to 10 hours, and the reaction temperature ranges from 80 to 200° C., preferably from 120 to 180° C.

The polyalkyl or polyalkylene succinic anhydrides group R consists of polyisobutylene, polybutene, polyethylene, or polypropylene derivatives and its molecular weight ranges from 450 to 5000 daltons; preferably, as an R substituent we have the polyisobutylene derivatives, with a molecular weight ranging from 450 to 2300. Typically, the polyalkylene succinic anhydrides are prepared as described in the MX 234498 national patent, as well as in the U.S. Pat. No. 3,361,673 and U.S. Pat. No. 3,676,089 United States patents, whereas the polyalkyl succinic anhydrides can be prepared by catalytically hydrogenating the corresponding polyalkylene succinic anhydrides, using palladium on carbon as a catalyst.

The 2-(aminoalkylamino)-2,3-disubstituted-alcohols preferred by the present invention include commercially available compounds or those which are easily prepared by conventional methods, such as:
2(-2-aminoethylamino)ethanol, 2-(3-aminopropylamino)ethanol, 2-(4-aminobutylamino)ethanol, 2-(5-aminopenty-

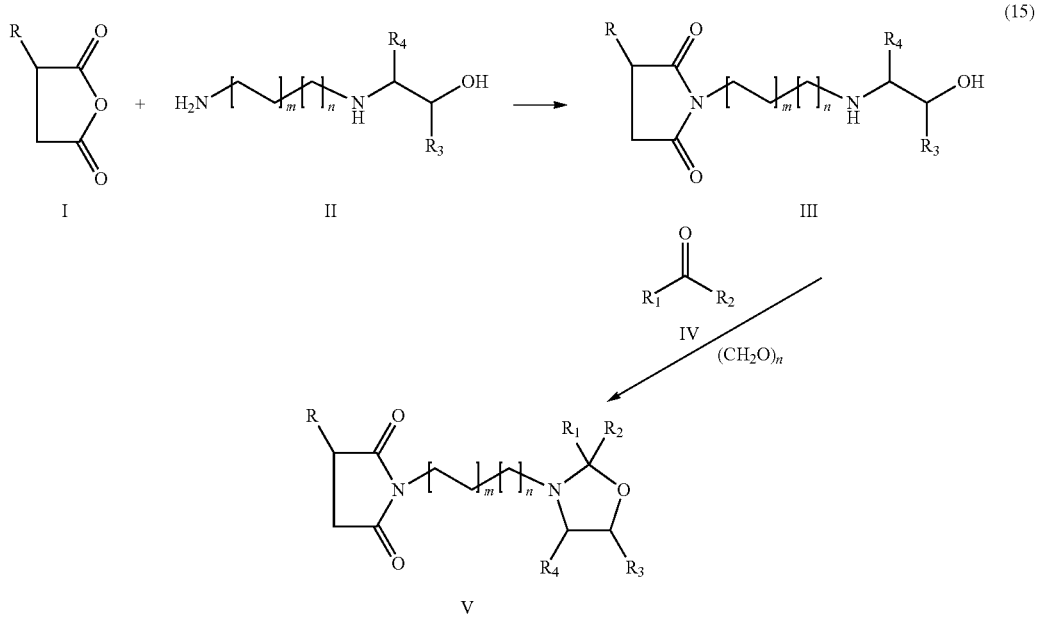

The first reaction stage of the synthesis pathway consists in reacting a polyalkyl or polyalkylene succinic anhydride having the formula I with a 2-(aminoalkylamino)-2,3-disubstituted-alcohol having the formula II, in order to obtain the corresponding polyalkyl or polyalkenyl N-hydroxyalkyl succinimide having the structural formula III.

lamino)ethanol, 2-(6-aminohexylamino)ethanol, 2-(7-aminoheptylamino)ethanol, 2-(8-aminooctylamino)ethanol, 2-(9-aminononylamino)ethanol, 2-(10-aminodecylamino) ethanol, 2-(2-aminoethylamino)-1,2-dimethyl-ethanol, 2-(2-aminoethylamino)-2-methyl-ethanol, 1-methyl-2-(2-aminoethylamino)-ethanol, 2-(2-aminoethylamino)-1,2-dyphenilethanol, 2-(2-aminoethylamino)-2-phenil-ethanol, 1-phenyl-2-(2-aminoethylamino)-ethanol, 2-hydroxy-3-(2-aminoethylamino)-propanol, and 2-hydroxymethyl-2-(2-aminoethylamino)ethanol.

The second reaction stage of the synthesis pathway consists in reacting the corresponding polyalkyl or polyalkenyl N-hydroxyalkyl succinimides with a compound having the structural formula IV, or paraformaldehyde, in order to obtain the corresponding oxazolidines derived from polyalkyl or polyalkenyl N-hydroxyalkyl succinimides with the structural formula V.

The compounds with the structural formula IV preferred by the present invention include commercially available aldehydes and ketones or those easily prepared using conventional methods. The polyalkyl or polyalkenyl N-hydroxyalkyl succinimide to aldehyde, ketone or paraformaldehyde molar ratio ranges from 1:1 to 1:5, preferably from 1:1 to 1:2, with the reaction being carried out in the bulk substance or in the presence of an inert hydrocarbon solvent, preferably toluene, mixtures of xylene, o-xylene, m-xylene, p-xylene, kerosene, and turbo-fuel. The reaction time depends on the structure of the polyalkyl or polyalkenyl N-hydroxyalkyl succinimide or the aldehyde or ketone used as reactants, as well as on the temperature and pressure at which the reaction is carried out. Generally, the reaction time ranges from 1 to 24 hours, preferably from 1 to 9 hours; the temperature ranges from 60 to 200° C., preferably from 100 to 180° C., and the pressure ranges from 60 to 760 mmHg, preferably from 400 to 585 mm of Hg.

The aldehydes and ketones preferred by the present invention include:
ethanal, propanal,
butanal, pentanal,
hexanal, heptanal,
octanal, nonyl aldehyde,
decyl aldehyde, dodecyl aldehyde,
tetradecyl aldehyde, hexadecyl aldehyde,
octadecyl aldehyde, benzaldehyde,
salicylaldehyde, 3-hydroxybenzaldehyde,
4-hydroxybenzaldehyde, o-tolualdehyde,
m-tolualdehyde, p-tolualdehyde,
o-anisaldehyde, m-anisaldehyde,
p-anisaldehyde, 4-ter-butylbenzaldehyde,
4-butylbenzaldehyde, 4-ethylbenzaldehyde,
2-ethylbenzaldehyde, 4-propylbenzaldehyde,
2-propylbenzaldehyde, 4-phenoxybenzaldehyde,
3-phenoxybenzaldehyde, 4-formyl-benzene sulfonic acid,
2-formyl-benzene sulfonic acid, 2-biphenyl carboxyaldehyde,
4-biphenyl carboxyaldehyde, 2,3-dihydroxybenzaldehyde,
2,4-dihydroxybenzaldehyde, 2,5-dihydroxybenzaldehyde,
3,4-dihydroxybenzaldehyde, 3,5-dihydroxybenzaldehyde,
2-hydroxy-4-methoxybenzaldehyde, 2-hydroxy-5-methoxybenzaldehyde,
3-hydroxy-4-methoxybenzaldehyde, 2-hydroxy-3-methylbenzaldehyde,
2-hydroxy-5-methylbenzaldehyde, 4-hydroxy-3-methylbenzaldehyde,
1-naphthaldehyde, 2-naphthaldehyde,
2-hydroxy-1-naphthaldehyde, 4-hydroxy-1-naphthaldehyde,
2-methyl-1-naphthaldehyde, 4-methyl-1-naphthaldehyde,
2-methoxy-1-naphthaldehyde, 4-methoxy-1-naphthaldehyde,
6-methoxy-2-naphthaldehyde, acetone,
2-butanone, benzophenone,
2,2'-dihydroxybenzophenone, 2,4-dihydroxybenzophenone,
acetophenone, and 4'-tert-butyl acetophenone.

The oxazolidines derived from polyalkyl or polyalkenyl N-hydroxyalkyl succinimides of the present invention are useful as additives to be added to hydrocarbon fuels, preferably in those hydrocarbon fuels having boiling points within the range of gasoline and diesel, to prevent and control the formation of deposits in internal combustion engines, particularly in intake valves. The concentration of additive required to control the formation of deposits depends on the type of fuel, the type of internal combustion engine, and the presence of other additives in the fuel.

In general, the concentration of the oxazolidines of the present invention in hydrocarbon fuels ranges from 50 to 2000 parts per million (ppm), preferably from 75 to 500 ppm. In the presence of other types of additives that control the deposition of organic compounds, a lesser amount of the oxazolidines of the present invention can be used.

The oxazolidines of the present invention can be formulated as a concentrate using inert organic solvents having a boiling point within the range of 75 to 200° C., preferably aromatic hydrocarbon solvents, such as benzene, toluene, mixtures of xylenes, o-xylene, m-xylene, p-xylene, branched and non-branched aliphatic alcohols with structures containing from 3 to 10 atoms, such as isoporopanol, butanol, and pentanol, as well as aromatic solvents mixtures with branched and non-branched aliphatic alcohols. The quantity of additive in the formulation ranges from 10 to 90 wt. %, preferably from 40 to 70 wt. %.

When the hydrocarbon fuel to be additivated is gasoline, other type of additives can be used in combination with the additive of the present invention, including: agents with anti-detonant properties, such as tert-butyl methyl ether (MTBE), tert-amyl methyl ether (TAME) and methylcyclopentadienyl manganese tricarbonyl; agents with corrosion-inhibitory properties, such as carboxylic acids and imidazolines; agents with detergent-dispersant properties, such as polyamines, poly(oxyalkylene) amines, poly(oxyalkylene) imidazolines, poly(oxyalkylene) succinimides, poly(oxyalkylene) aminocarbamates and succinimides; agents with antioxidant properties, such as catechols; agents with de-emulsifying properties, such as ethylene oxide- and propylene oxide-derived copolymers; and agents with metal-sequestrating properties, such as salicylaldehyde-derived imines.

In case the fuel to be additivated is diesel, agents such as pour point depressants and cetane index boosters can be used in combination with the additive of the present invention.

Natural or synthetic compounds with fluidizing properties, such as mineral oil, refined petroleum oils, polyalkanes, polyalkenes, polyethers, and polyesters, can also be used in combination with the additive of the present invention, which may show synergistic effects on the ability to control and prevent the deposition of organic compounds when used mixed with fluidizing agents. Fluidizing agents are typically used in hydrocarbon fuels at concentrations ranging from 20 to 1000 ppm, preferably from 20 to 100 ppm. The fluidizing agent-to-additive ratio that prevents and controls the deposition of organic compounds ranges from 1:10 to 10:1, preferably from 1:7 to 3:1.

Following, we describe some practical examples in order to have a better understanding of the present invention, without this limiting its scope.

Example 1

Preparation of:

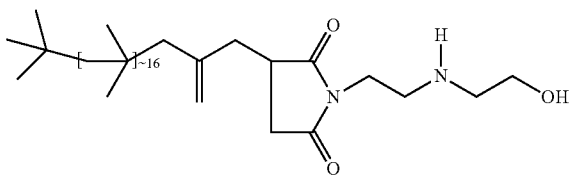

250 grams of polyisobutylene succinic anhydride (0.23 moles, polyisobutylene-derived, having an average molecular weight of 1000 and an 88% methylvinylidene content) were mixed with 23.9 grams of 2-(2-aminoethylamino) ethanol (0.23 moles) in a 500 ml three-neck round-bottom flask, equipped with a magnetic stirrer, a Dean Stark trap, a cooling device, and a thermometer, at room temperature and under a nitrogen atmosphere. The temperature of the reaction mixture was increased gradually up to 130° C. and the absolute pressure of the system was brought from atmospheric pressure up to 450 mmHg; the reaction mixture was kept under these conditions for one hour, then the system was brought to room temperature and pressure, obtaining as a product 268 grams of a viscous oil, which was characterized by $^{13}C$ nuclear magnetic resonance (NMR) and infrared (IR) spectroscopy. The $^{13}C$ NMR spectra were obtained in a 200 MHz machine, using deuterated chloroform ($CDCl_3$) and tetramethylsilane as dissolvent and reference, respectively.

$^{13}C$ NMR representative chemical shifts in ppm: 31.22, 32.43, 38.11, 59.50, 115.94, 143.87, 177.13, 180.13.

IR representative bands ($cm^{-1}$, film): 3363, 2950, 2895, 1773, 1702, 1471, 1391, 1365, 1229.

Example 2

Preparation of:

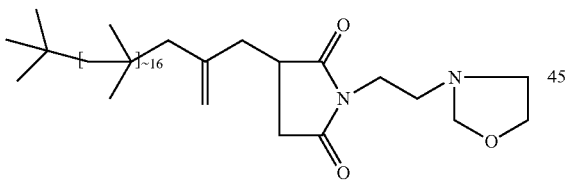

250 grams of the polyalkenyl N-hydroxyalkyl succinimide described in Example 1 (0.21 moles) were mixed with 6.3 grams of paraformaldehyde (0.21 moles) in a 500 ml three-neck round-bottom flask equipped with a magnetic stirrer, a Dean Stark trap, a cooling device, and a thermometer, at room temperature and under a nitrogen atmosphere. The temperature of the reaction mixture was increased gradually up to 140° C., and the absolute temperature of the system was brought from atmospheric pressure up to 585 mmHg; the reaction mixture was maintained under these conditions for half an hour, then the system was brought to room temperature and pressure, obtaining as a product 251.1 grams of a viscous oil, which was characterized by $^{13}C$ NMR and IR spectroscopy.

$^{13}C$ NMR representative chemical shifts ($CDCl_3$), 200 MHz, δ (ppm): 30.74, 31.19, 32.40, 38.0, 59.43, 86.76, 143.5, 176.56, 179.57.

IR representative bands ($cm^{-1}$, film): 2951, 2893, 1774, 1742, 1470, 1390, 1365, 1228, 1145, 1065.

Example 3

Preparation of:

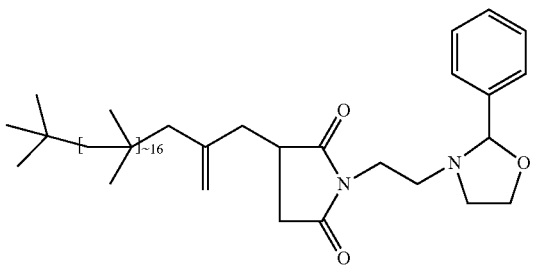

250 grams of the polyalkenyl N-hydroxyalkyl succinimide described in Example 1 (0.21 moles) were mixed with 22.3 grams of benzaldehyde (0.21 moles), stirring vigorously at room temperature and pressure. The temperature of the reaction mixture was increased gradually up to 120° C., and the absolute pressure of the system was brought up to 450 mmHg; the reaction mixture was maintained under these conditions for one hour, then the system was brought to room temperature and pressure, obtaining as a product 262.3 grams of a viscous oil, which was characterized by $^{13}C$ NMR and IR spectroscopy.

$^{13}C$ NMR representative chemical shifts ($CDCl_3$), 200 MHz, δ (ppm): 30.77, 31.21, 32.41, 38.10, 59.47, 96.70, 127.44, 128.20, 143.65, 176.24, 179.51.

IR representative bands ($cm^{-1}$, film): 2951, 2893, 1775, 1706, 1471, 1391, 1365, 1230, 1065, 788, 756.

Example 4

Preparation of:

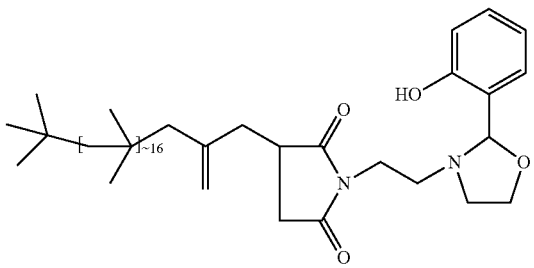

250 grams of the polyalkenyl N-hydroxyalkyl succinimide described in Example 1 (0.21 moles) were mixed with 25.6 grams of salicylaldehyde (0.21 moles), stirring vigorously at room temperature and pressure. The temperature of the reaction mixture was gradually increased up to 130° C., and the absolute pressure of the system was brought up to 500 mmHg; the reaction mixture was maintained under these conditions for two hours, then the system was brought to room temperature and pressure, obtaining as a product 264.5 grams of a viscous oil, which was characterized by $^{13}C$ NMR and IR spectroscopy.

$^{13}C$ NMR representative chemical shifts ($CDCl_3$), 200 MHz, δ (ppm): 30.77, 31.27, 32.43, 38.1, 59.48, 97.51, 119.41, 130.96, 176.91, 179.91.

IR representative bands (cm$^{-1}$, film): 2951, 2895, 1774, 1705, 1471, 1391, 1365, 1230, 1156, 756.

Example 5

Preparation of:

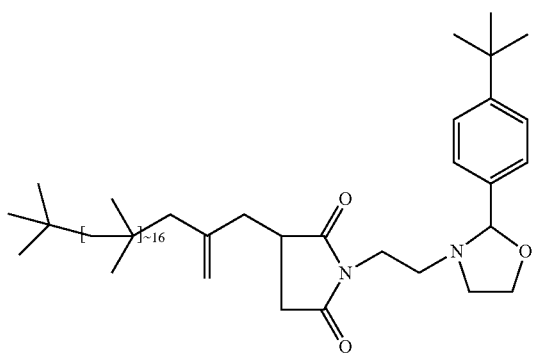

250 grams of the polyalkenyl N-hydroxyalkyl succinimide described in Example 1 (0.21 moles) were mixed with 34.1 grams of 4-tert-butylbenzaldehyde (0.21 moles) stirring vigorously at room temperature and pressure. The temperature of the reaction mixture was gradually increased up to 160° C., and the absolute pressure of the system was brought up to 400 mmHg; the reaction mixture was maintained under these conditions for three hours; afterwards, the system was brought to room temperature and pressure, obtaining as a product 274.3 grams of a viscous oil, which was characterized by $^{13}$C NMR and IR spectroscopy.

$^{13}$C NMR representative chemical shifts (CDCl$_3$), 200 MHz, δ (ppm): 30.77, 31.21, 31.35, 32.42, 38.11, 59.49, 96.70, 126.14, 127.10, 143.66, 176.31, 179.45.

IR representative bands (cm$^{-1}$, film): 2952, 2895, 1775, 1707, 1472, 1392, 1365, 1230, 1167, 1109, 824, 792.

Example 6

Preparation of:

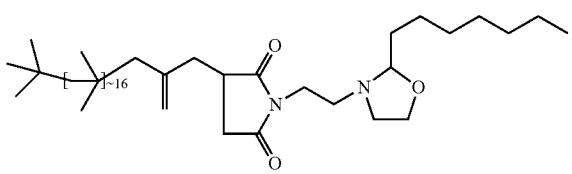

250 grams of the polyalkenyl N-hydroxyalkyl succinimide described in Example 1 (0.21 moles) were mixed with 26.9 grams of octanal (0.21 moles), stirring vigorously at room temperature and pressure. The temperature of the reaction mixture was gradually increased up to 100° C., and the absolute pressure of the system was brought up to 585 mmHg; the reaction mixture was maintained under these conditions for three hours, then the system was brought to room temperature and pressure, obtaining as a product 269.1 grams of a viscous oil, which was characterized by $^{13}$C NMR and IR spectroscopy.

$^{13}$C NMR representative chemical shifts (CDCl$_3$), 200 MHz, δ (ppm): 14.13, 22.65, 31.22, 32.43, 38.12, 59.50, 96.27, 115.95, 143.61, 176.47, 179.68.

IR representative bands (cm$^{-1}$, film): 2951, 2894, 1776, 1708, 1471, 1392, 1365, 1229, 1149.

Example 7

Preparation of:

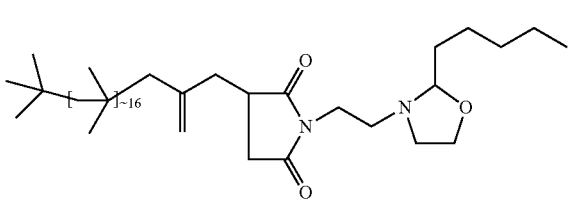

250 grams of the polyalkenyl N-hydroxyalkyl sucinimide described in Example 1 (0.21 moles) were mixed with 21 grams of hexanal (0.21 moles), stirring vigorously at room temperature and pressure. The temperature of the reaction mixture was gradually increased up to 80° C., and the absolute pressure of the system was brought up to 585 mmHg; the reaction mixture was maintained under these conditions for three hours, then the system was brought to room temperature and pressure, obtaining as a product 262 grams of a viscous oil, which was characterized by $^{13}$C NMR and IR spectroscopy.

$^{13}$C NMR representative chemical shifts (CDCl$_3$), 200 MHz, δ (ppm): 30.80, 31.21, 32.41, 38.10, 59.46, 96.22, 116.0, 135.42, 143.55, 176.64, 179.93.

IR representative bands (cm$^{-1}$, film): 2949, 2891, 1775.4, 1707, 1468, 1391, 1365, 1229, 1150, 1045.

Example 8

Preparation of:

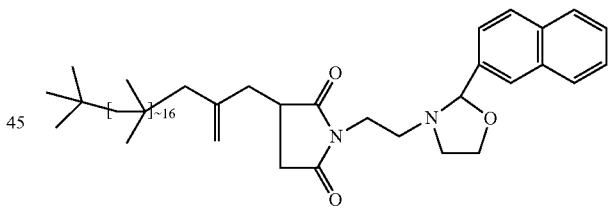

250 grams of the polyalkenyl N-hydroxyalkyl succinimide described in Example 1 (0.21 moles) were mixed with 32.8 grams of 2-naphthaldehyde (0.21 moles), stirring vigorously at room temperature and pressure. The temperature of the reaction mixture was gradually increased up to 160° C., and the absolute pressure of the system was brought up to 400 mmHg; the reaction mixture was maintained under these conditions for five hours, then the system was brought to room temperature and pressure, obtaining as a product 276.1 grams of a viscous oil, which was characterized by $^{13}$C NMR and IR spectroscopy.

$^{13}$C NMR representative chemical shifts (CDCl$_3$), 200 MHz, δ (ppm): 30.78, 31.22, 32.43, 38.12, 59.50, 96.89, 114.39, 124.76, 126.11, 128.04, 132.95, 135.46, 176.25, 179.50.

IR representative bands (cm$^{-1}$, film): 2951, 2893, 1775, 1706, 1472, 1392, 1365, 1229, 1169, 1138, 819, 745.

Example 9

Preparation of:

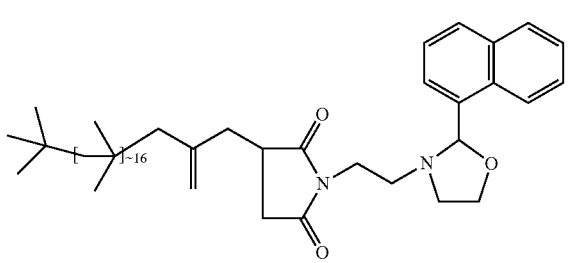

250 grams of the polyalkenyl N-hydroxyalkyl succinimide described in Example 1 (0.21 moles) were mixed with 32.8 grams of 1-naphthaldehyde (0.21 moles), stirring vigorously at room temperature and pressure. The temperature of the reaction mixture was gradually increased up to 160° C., and the absolute pressure of the system was brought up to 400 mmHg; the reaction mixture was maintained under these conditions for five hours, then the system was brought to room temperature and pressure, obtaining as a product 275.3 grams of a viscous oil, which was characterized by $^{13}$C NMR and IR spectroscopy.

$^{13}$C NMR representative chemical shifts (CDCl$_3$), 200 MHz, δ (ppm): 30.71, 31.22, 32.43, 38.11, 59.49, 124.93, 126.90, 131.36, 134.20, 176.35, 179.55.

IR representative bands (cm$^{-1}$, film): 2951, 2893, 1775, 1706, 1472, 1392, 1365, 1229, 1168, 1139, 799, 780.

Example 10

Preparation of:

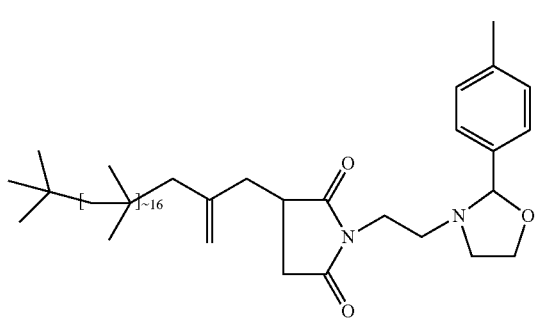

250 grams of the polyalkenyl N-hydroxyalkyl succinimide described in Example 1 (0.21 moles) were mixed with 25.3 grams of p-tolualdehyde (0.21 moles), stirring vigorously at room temperature and pressure. The temperature of the reaction mixture was gradually increased up to 110° C., and the absolute pressure of the system was brought up to 550 mmHg; the reaction mixture was maintained under these conditions for two hours; then the system was brought to room temperature and pressure, obtaining as a product 268.5 grams of a viscous oil, which was characterized by $^{13}$C NMR and IR spectroscopy.

$^{13}$C NMR representative chemical shifts (CDCl$_3$), 200 MHz, δ (ppm): 21.80, 30.75, 31.35, 32.40, 38.25, 59.45, 59.50, 128.75, 129.50, 144.5, 176.20, 179.35.

IR representative bands (cm$^{-1}$, film): 2951, 2893, 1775, 1707, 1473, 1392, 1229, 1168, 1139, 799.

Example 11

Preparation of:

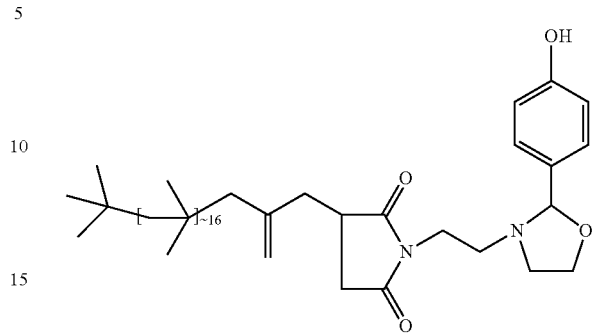

250 grams of the polyalkenyl N-hydroxyalkyl succinimide described in Example 1 (0.21 moles) were mixed with 25.6 grams of 4-hydroxybezaldehyde (0.21 moles), stirring vigorously at room temperature and pressure. The temperature of the reaction mixture was gradually increased up to 130° C., and the absolute pressure of the system was brought up to 500 mmHg; the reaction mixture was maintained under these conditions for two hours, then the system was brought to room temperature and pressure, obtaining as a product 266.4 grams of a viscous oil, which was characterized by $^{13}$C NMR and IR spectroscopy.

$^{13}$C NMR representative chemical shifts (CDCl$_3$), 200 MHz, δ (ppm): 30.78, 31.21, 32.42, 38.11, 59.49, 96.48, 129.0, 132.44, 135.46, 176.20, 179.35.

IR representative bands (cm$^{-1}$, film): 3465.46, 2951, 2894, 1775, 1707, 1472, 1391, 1365, 1229, 811.

Example 12

Preparation of:

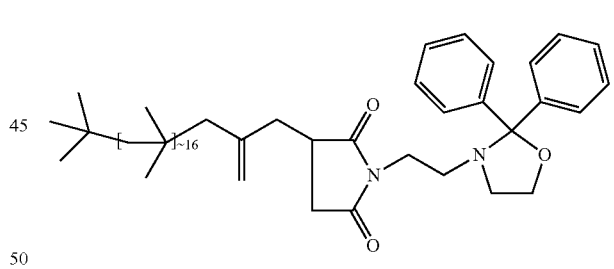

250 grams of the polyalkenyl N-hydroxyalkyl succinimide described in Example 1 (0.21 moles) were mixed with 38.3 grams of benzophenone (0.21 moles), stirring vigorously at room temperature and pressure. The temperature of the reaction mixture was gradually increased up to 160° C., and the absolute pressure of the system was brought up to 300 mmHg; the reaction mixture was maintained under these conditions for seven hours, then the system was brought to room temperature and pressure, obtaining as a product 279.5 grams of a viscous oil, which was characterized by $^{13}$C NMR and IR spectroscopy.

$^{13}$C NMR representative chemical shifts (CDCl$_3$), 200 MHz, δ (ppm): 30.65, 31.09, 32.29, 38.00, 59.37, 96.5, 128.11, 129.91, 132.25, 132.34, 177.0, 179.9.

IR representative bands (cm$^{-1}$, film): 2950, 2895, 1774, 1702, 1471, 1390, 1366, 1230, 701.

Example 13

Preparation of:

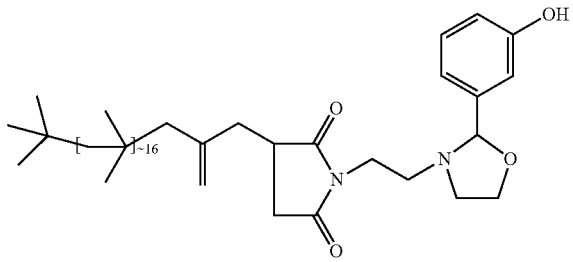

250 grams of the polyalkenyl N-hydroxyalkyl succinimide described in Example 1 (0.21 moles) were mixed with 25.6 grams of 3-hydroxybenzaldehyde (0.21 moles) and 250 grams of a mixture of ortho-, meta- and para-xylenes, in a 1000 ml three-neck round-bottom flask, equipped with a magnetic stirrer, a Dean Stark trap, a cooling device, and a thermometer, stirring vigorously at room temperature. The temperature of the reaction mixture was raised until the reflux-temperature of the system was reached, time at which an amber-colored substance was obtained; the reaction temperature was maintained under these conditions for a period of two hours, then the system was brought to room temperature and the xylene mixture used as solvent was distilled at an absolute pressure of 3 mmHg. 265.6 grams of a viscous oil were obtained as a product, which was characterized by $^{13}C$ NMR and IR spectroscopy.

$^{13}C$ NMR representative chemical shifts ($CDCl_3$), 200 MHz, δ (ppm): 30.77, 31.22, 32.42, 38.13, 59.51, 96.40, 129.44, 135.50, 141.41, 176.89, 179.90.

IR representative bands ($cm^{-1}$, film): 2951, 2894, 1773, 1700, 1470, 1391, 1365, 1229, 1168, 783.

Example 14

Performance Tests of the Oxazolidines Derived from Polyalkyl or Polyalkenyl N-Hydroxyalkyl Succinimides of the Present Invention, in a Single-Cylinder Engine The oxazolidines derived from polyalkyl or polyalkenyl N-hydroxyalkyl succinimides of the present invention were dosed, at different concentrations in ppm, to a Mexican gasoline PEMEX-Magna-type, and their capacity to reduce the deposits in intake valves was measured through a performance test with a single-cylinder engine. A Kohler 4 HP, natural aspiration, spark plug ignition, and air-cooled single-cylinder engine was used for the test. Each run had a duration time of 16 hours, and the speed of the engine was adjusted at 2100 rpm±100. The amount of deposits obtained in the intake valve was quantified in milligrams, and the efficiency of the additive was measured using the deposits obtained with a non-additivated gasoline as a reference. Additionally, in order to demonstrate the technical advantages of the compounds object of the present invention, comparative tests were performed taking as a reference the hydroxylated polyisobutenyl succinimide and the corresponding formulation, which is object of the MX 234,498 national patent.

The results obtained in the performance tests for each oxazolidine are shown in Tables 1 to 10; whereas Tables 11 to 12 show the results obtained for the compounds and formulation protected in the MX 234,498 patent.

TABLE 1

| | Intake valve deposit weight (mg) | | | |
|---|---|---|---|---|
| Sample[1] | Run 1 | Run 2 | Average | Efficiency |
| Base fuel | 6.80 | 6.70 | 6.75 | 0 |
| Example 2 oxazolidine | 0.50 | 0.60 | 0.55 | 91.9 |

[1]At 85 ppm actives

TABLE 2

| | Intake valve deposit weight (mg) | | | |
|---|---|---|---|---|
| Sample[1] | Run 1 | Run 2 | Average | Efficiency |
| Base fuel | 7.10 | 6.90 | 7.00 | 0 |
| Example 2 oxazolidine | 0.20 | 0.30 | 0.25 | 96.4 |

[1]At 120 ppm actives

TABLE 3

| | Intake valve deposit weight (mg) | | | |
|---|---|---|---|---|
| Sample[1] | Run 1 | Run 2 | Average | Efficiency |
| Base fuel | 5.40 | 5.70 | 5.55 | 0 |
| Example 2 oxazolidine | 0.60 | 0.70 | 0.65 | 88.3 |

[1]At 75 ppm actives

TABLE 4

| | Intake valve deposit weight (mg) | | | |
|---|---|---|---|---|
| Sample[1] | Run 1 | Run 2 | Average | Efficiency |
| Base fuel | 6.00 | 5.90 | 5.95 | 0 |
| Example 2 oxazolidine | 1.00 | 0.90 | 0.95 | 84.0 |

[1]At 65 ppm actives

TABLE 5

| | Intake valve deposit weight (mg) | | | |
|---|---|---|---|---|
| Sample[1] | Run 1 | Run 2 | Average | Efficiency |
| Base fuel | 7.10 | 7.00 | 7.05 | 0 |
| Example 2 oxazolidine | 0.40 | 0.50 | 0.45 | 93.6 |

[1]At 85 ppm actives, 30 ppm of polyisobutylene having an average of 16 isobutylene units and 50 ppm of xylene mixture.

TABLE 6

| | Intake valve deposit weight (mg) | | | |
|---|---|---|---|---|
| Sample[1] | Run 1 | Run 2 | Average | Efficiency |
| Base fuel | 5.40 | 5.40 | 5.40 | 0 |
| Example 2 oxazolidine | 0.80 | 0.70 | 0.75 | 86.1 |

[1]At 75 ppm actives, 30 ppm of polyisobutylene having an average of 16 isobutylene units, 14 ppm of propylene polyoxide having an average of 16 propylene oxide units and structural characteristics as those mentioned in the MX 234498 national patent and 33 ppm of xylene mixture.

TABLE 7

| | Intake valve deposit weight (mg) | | | |
|---|---|---|---|---|
| Sample[1] | Run 1 | Run 2 | Average | Efficiency |
| Base fuel | 5.80 | 6.00 | 5.90 | 0 |
| Example 2 oxazolidine | 0.90 | 1.00 | 0.95 | 83.9 |

[1]At 65 ppm actives, 30 ppm of polyisobutylene having an average of 16 isobutylene units, 14 ppm of propylene polyoxide having an average of 16 propylene oxide units and structural characteristics as those mentioned in the MX 234498 national patent and 33 ppm of xylene mixture.

TABLE 8

| | Intake valve deposit weight (mg) | | | |
|---|---|---|---|---|
| Sample[1] | Run 1 | Run 2 | Average | Efficiency |
| Base fuel | 6.80 | 6.70 | 6.75 | 0 |
| Example 3 oxazolidine | 1.10 | 0.90 | 1.00 | 85.2 |

[1]At 85 ppm actives

TABLE 9

| | Intake valve deposit weight (mg) | | | |
|---|---|---|---|---|
| Sample[1] | Run 1 | Run 2 | Average | Efficiency |
| Base fuel | 7.10 | 6.90 | 7.00 | 0 |
| Example 4 oxazolidine | 1.30 | 1.10 | 1.15 | 83.5 |

[1]At 85 ppm actives

TABLE 10

| | Intake valve deposit weight (mg) | | | |
|---|---|---|---|---|
| Sample[1] | Run 1 | Run 2 | Average | Efficiency |
| Base fuel | 6.90 | 6.70 | 6.80 | 0 |
| Example 7 oxazolidine | 0.6 | 0.5 | 0.55 | 91.9 |

[1]At 85 ppm actives

TABLE 11

| | Intake valve deposit weight (mg) | | | |
|---|---|---|---|---|
| Sample[1] | Run 1 | Run 2 | Average | Efficiency |
| Base fuel | 7.10 | 6.90 | 7.00 | 0 |
| MX 234,498 Patent Hydroxylated polyisobutenyl succinimide (n = 23.75) | 1.9 | 2.1 | 2.00 | 71.4 |

[1]At 120 ppm actives

TABLE 12

| | Intake valve deposit weight (mg) | | | |
|---|---|---|---|---|
| Sample[1] | Run 1 | Run 2 | Average | Efficiency |
| Base fuel | 7.00 | 6.90 | 7.00 | 0 |
| MX 234,498 patent Formulation 4 (n = 23.75) | 1.2 | 1.1 | 1.15 | 83.6 |

[1]At 120 ppm actives; 16.5 ppm of propylene polyoxide having an average of 16 propylene oxide units The comparison of the results obtained with the Example 2 (Tables 1 to 6) and Example 7 oxazolidines versus those obtained with the Hydroxylated polyisobutenyl succinimide (Table 11) and Formulation 4 (Table 12) from the MX 234,498 patent, show that the compounds of the present invention offer considerable technical advantage.

That which is claimed is:

1. An ash less detergent/dispersant additive formulation comprising an oxazolidine derived from polyalkenyl N-hydroxyalkyl succinimides as a main active component, and an inert organic solvent, said oxazolidine having the formula:

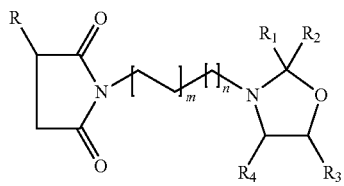

wherein:

R is a polyalkenyl group having an average molecular weight ranging from 450 to 5000 daltons;

m is an integer between 1 and 5;

n is an integer between 0 and 1; and $R_1$, $R_2$ are H, $R_3$, and $R_4$ are independent radicals, represented by the groups: —H, —$CH_2(CH_2)_A$B, —$C_6H_3$DE or —$C_{10}H_4$FG; wherein:

A is an integer between 0 and 8,

B is a group selected among —H, —$NH_2$, —OH, —COOH, and

D, E, F, and G are independent radicals selected among the groups: —H, —$CH_3$, —$CH_2CH_3$, —$CH_2CH_2CH_3$, —$CH_2(CH_2)_2CH_3$, —$(CH_3)_3$, $C_6H_5$, —$NH_2$, —OH, —$OCH_3$, $OCH_2CH_2OH$, $OCH(CH_3)CH_2OH$, $OC_6H_5$—COOH, —$SO_3$, wherein said additive formulation inhibits precipitation and disperses heavy organic compounds in gasoline.

2. The ash less detergent/dispersant additive formulation derived from polyalkenyl N-hydroxyalkyl succinimides according to claim 1, wherein group R is a polyisobutylene derivative having an average molecular weight ranging from 450 to 5000 daltons.

3. The ash less detergent/dispersant additive formulation derived from polyalkenyl N-hydroxyalkyl succinimides according to claim 1, wherein the substituents $R_3$ and $R_4$ are derived from a 2-(aminoalkylamino)-2,3-disubstituted-alcohol.

4. The ash less detergent/dispersant additive formulation derived from polyalkenyl N-hydroxyalkyl succinimides according to claim 1, wherein the sum of m and n is an even number.

5. A process to obtain the oxazolidines derived from polyalkenyl N-hydroxyalkyl succinimides and paraformaldehyde from claim 1, represented by the following synthesis pathway:

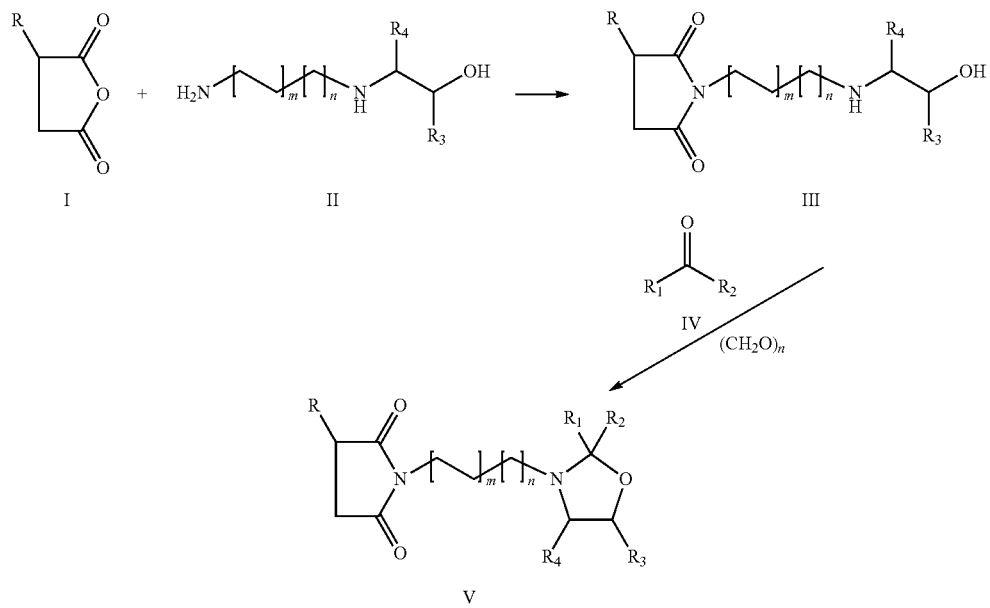

which consists of two reaction stages:

1) The first reaction stage comprises reacting a polyalkylene succinic anhydride having the formula I with a 2-(aminoalkylamino)-2,3-disubstituted-alcohol having the formula II to obtain the corresponding polyalkenyl N-hydroxyalkyl succinimide having the structural formula III, II) The second reaction stage comprises reacting the corresponding polyalkenyl N-hydroxyalkyl succinimides of formula III with paraformaldehyde to obtain the corresponding oxazolidines derived from polyalkenyl N-hydroxyalkyl succinimides having the structural formula V.

6. A process of synthesis according to claim 5, where, the polyalkyl or polyalkenyl N-hydroxyalkyl succinimide to paraformaldehyde molar ratio is 1:1.

7. A process of synthesis according to claim 6, wherein the reaction is carried out in the bulk substance without a solvent.

8. A process of synthesis according to claim 6, wherein the time of reaction is one half hour.

9. A process of synthesis according to claim 6, wherein the reaction temperature 140° C.

10. A process of synthesis according to claim 6, wherein the pressure at which the reaction is carried out is 585 mmHg.

11. A method of preventing or reducing build-up of organic deposits in an internal combustion engine using gasoline, said method comprising adding an oxazolidine to the gasoline at concentrations ranging from 50 to 2000 ppm, wherein said oxazolidines is derived from polyalkenyl N-hydroxyalkyl succinimides and paraformaldehyde and has the structural formula:

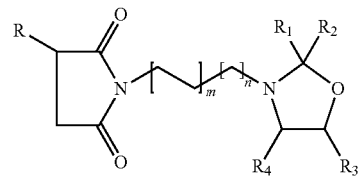

wherein:
R is a polyalkenyl group having an average molecular weight ranging from 450 to 5000 daltons;
m is an integer between 1 and 5;
n is an integer between 0 and 1; and
$R_1$, $R_2$ are H, $R_3$, and $R_4$ are independent radicals, represented by the groups: —H, —$CH_2(CH_2)_4$B, —$C_6H_3$DE or —$C_{10}H_4$FG; wherein:
A is an integer between 0 and 8,
B is a group selected among —H, —$NH_2$, —OH, —COOH, and
D, E, F and G are independent radicals selected from the group consisting of —H, —$CH_3$, —$CH_2CH_3$, —$CH_2CH_2CH_3$, —$CH_2(CH_2)_2CH_3$, —$(CH_3)_3$, —$C_6H_5$, —$NH_2$, —OH, —$OCH_3$, $OCH_2CH_2OH$, —$OCH(CH_3)CH_2OH$, —$OC_6H_5$—COOH and —$SO_3$.

12. The method according to claim 11, wherein said oxazolidines are added to the gasoline as a concentrate in inert organic solvents having a boiling within the range of 75 to 200° C., selected from the group consisting of mixtures of xylenes, o-xylene, m-xylene, and p-xylene, branched and non-branched aliphatic alcohols containing from 3 to 10 carbon atoms and mixtures of aromatic solvents with branched and non-branched aliphatic alcohols, where said concentrate contains 10 to 90 wt. % of said oxazolidine.

13. The method according to claim 11, wherein said gasoline further contains polyether compounds having fluidizing properties.

14. The method according to claim 13, wherein the fluidizing compounds are used in the hydrocarbon fuel at concentrations ranging from 10 to 1,000 ppm.

15. The method according to claim 14, wherein the ratio of fluidizing compounds to oxazolidines ranges from 1:10 to 10:1.

16. The process according to claim 5, wherein the reactions are carried out in the bulk substance without a solvent.

17. The process according to claim 5, wherein the time of reaction ranges from 0.5 to 1 hour.

18. The process according to claim 5, wherein the reaction temperature ranges from 140° C.

19. The oxazolidines of claim 1, wherein R is a polyisobutylene derivative having an average molecular weight of 450 to 2300 Daltons.

20. The oxazolidines of claim 1, wherein $R_3$ is $C_6H_3DE$ or $C_{10}H_4FG$.

21. The oxazolidines of claim 1, wherein $R_4$ is $C_6H_3DE$ or $C_{10}H_4FG$.

22. The method of claim 11, wherein said oxazolidine is added in an amount of 75 to 500 ppm based on the amount of the gasoline.

\* \* \* \* \*